(12) United States Patent
Daynes

(10) Patent No.: US 9,987,498 B2
(45) Date of Patent: Jun. 5, 2018

(54) MEDICAL DEVICE WITH INTERACTIVE CONTROL PANEL

(75) Inventor: John C. Daynes, Redmond, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 0 days. days.

(21) Appl. No.: 13/589,906

(22) Filed: Aug. 20, 2012

(65) Prior Publication Data

US 2014/0052201 A1 Feb. 20, 2014

(51) Int. Cl.
*A61N 1/362* (2006.01)
*A61N 1/39* (2006.01)
*A61N 1/04* (2006.01)

(52) U.S. Cl.
CPC ........... *A61N 1/3993* (2013.01); *A61N 1/046* (2013.01); *A61N 1/3925* (2013.01); *A61N 1/3987* (2013.01)

(58) Field of Classification Search
CPC ..... A61N 1/3993; A61N 1/3968; A61N 1/046
USPC .......................................................... 607/5
See application file for complete search history.

(56) References Cited

U.S. PATENT DOCUMENTS

| | | | |
|---|---|---|---|
| 5,200,913 A * | 4/1993 | Hawkins ............... | G06F 1/1615 345/168 |
| 5,868,794 A | 2/1999 | Barkley et al. | |
| 6,754,526 B2 * | 6/2004 | Daynes et al. .................... 607/5 | |
| 8,914,104 B2 * | 12/2014 | Kubat et al. ....................... 607/5 | |
| 2003/0208237 A1 | 11/2003 | Locke et al. | |
| 2003/0233129 A1 * | 12/2003 | Matos ............................... 607/5 | |
| 2005/0010258 A1 * | 1/2005 | Peterson et al. ................ 607/32 | |
| 2011/0130799 A1 | 6/2011 | Kubat et al. | |

FOREIGN PATENT DOCUMENTS

| | | |
|---|---|---|
| WO | 200238215 | 5/2002 |
| WO | WO 2008109615 A1 * | 9/2008 |
| WO | 2011066574 | 6/2011 |

OTHER PUBLICATIONS

International Search Report and Written Opinion, PCT/US2013/055615, dated Dec. 5, 2013, 11 pages.

* cited by examiner

*Primary Examiner* — Michael D Abreu
(74) *Attorney, Agent, or Firm* — Lane Powell PC

(57) ABSTRACT

Medical devices and methods in which a user can treat a patient or monitor a parameter of the patient or both may include a housing, a patient module located within the housing that is used for treating the patient, monitoring the patient or both, and a control panel. The control panel is attached to the housing and has a first surface and a second surface and is positionable between a first position and a second position with respect to the housing. The first position exposes a user to a first surface of the control panel and the second position exposes the user to a second surface of the control panel. A first set of user controls are located on one or the other of the first surface and the second surface and are structured to allow the user to interact with the patient module.

18 Claims, 10 Drawing Sheets

MEDICAL DEVICE WITH CONTROL PANEL IN OPEN POSITION

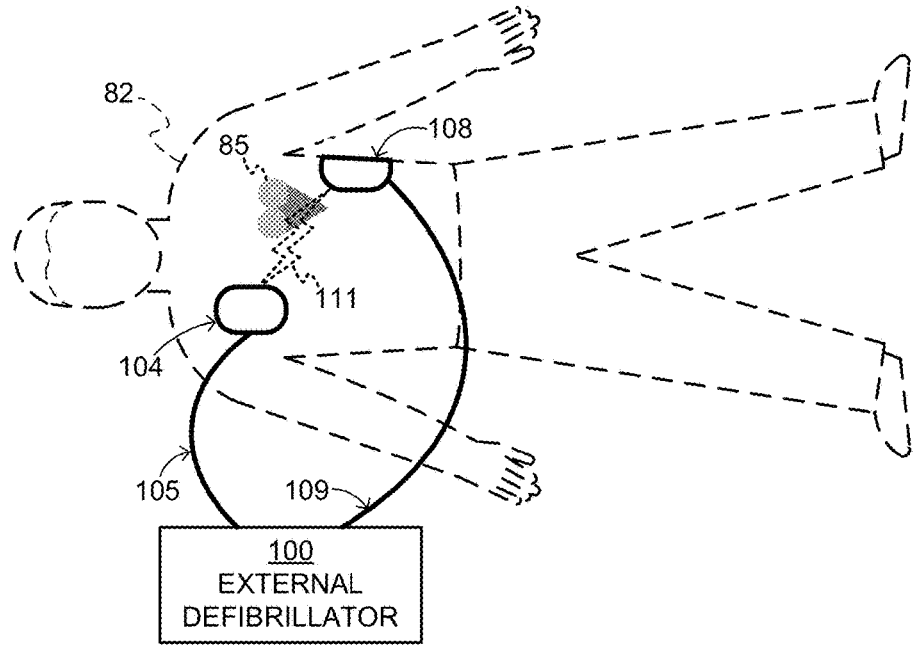
FIG. 1  *DEFIBRILLATION SCENE*
| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2  *TWO MAIN TYPES OF EXTERNAL DEFIBRILLATORS*

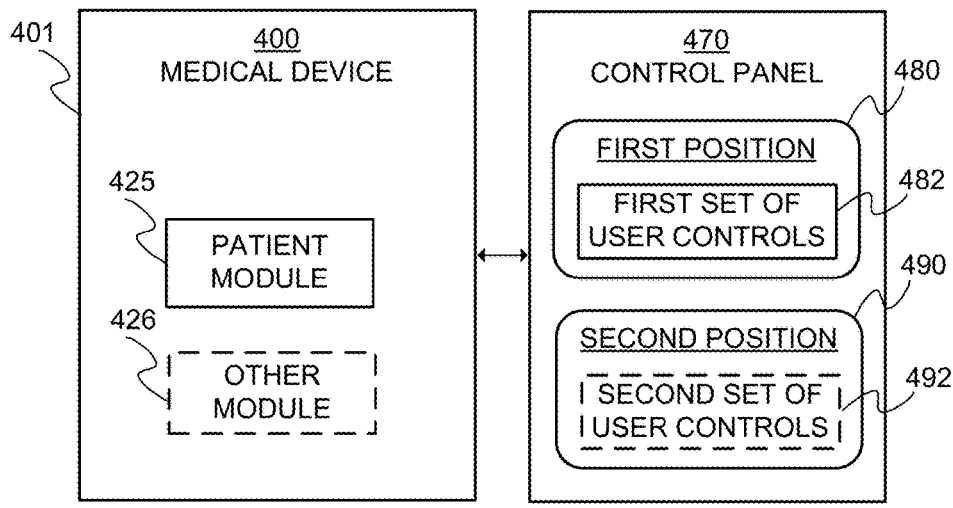
FIG. 4  MEDICAL DEVICE AND CONTROL PANEL
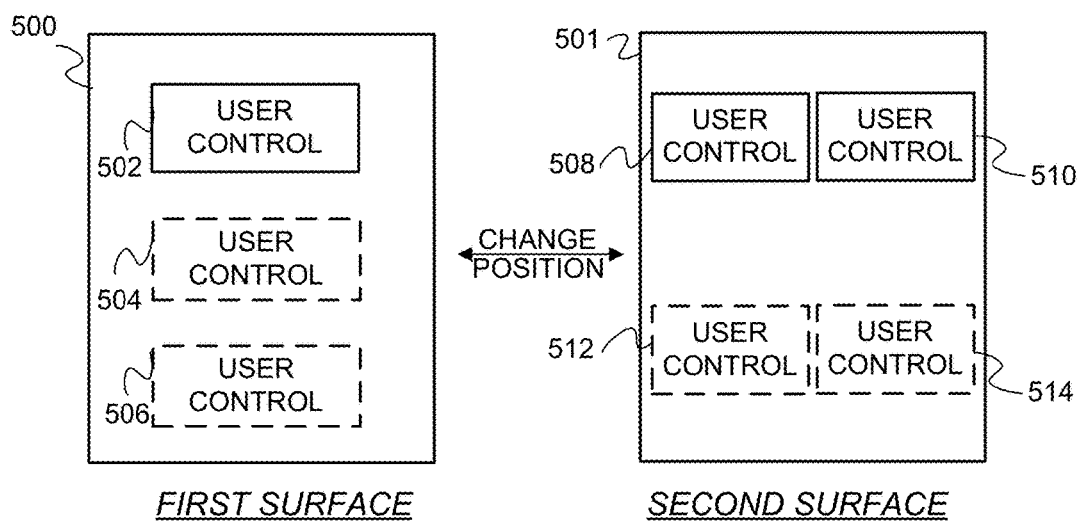
FIG. 5  FIRST AND SECOND SURFACES OF CONTROL PANEL

*MEDICAL DEVICE AND CONTROL PANEL COUPLED WITH CABLE*

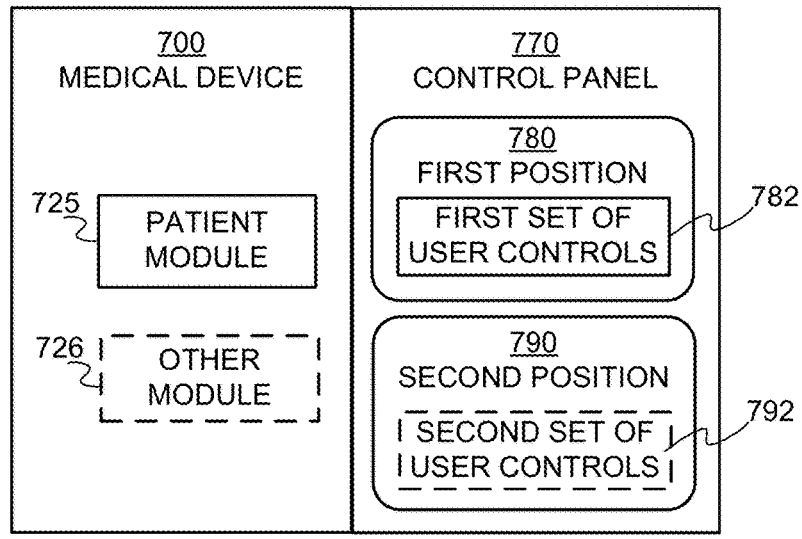
FIG. 7  *MEDICAL DEVICE AND ATTACHED CONTROL PANEL*
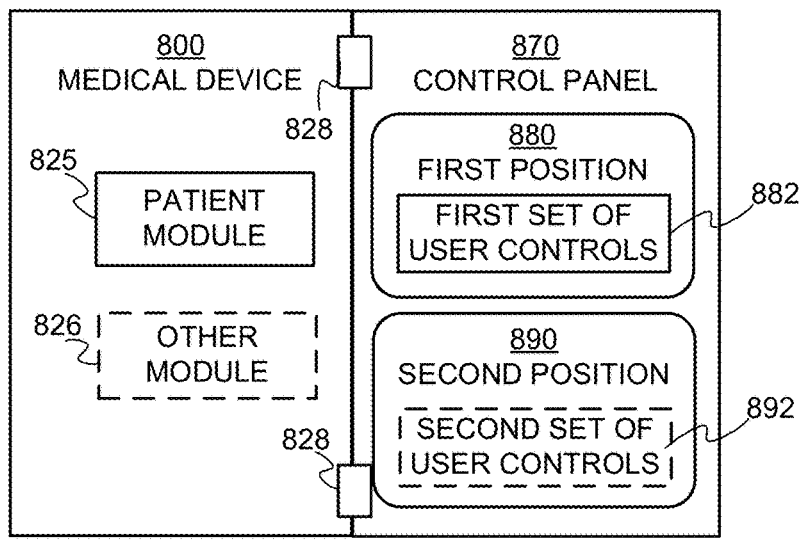
FIG. 8  *MEDICAL DEVICE AND HINGED CONTROL PANEL*

*MEDICAL DEVICE AND CONTROL PANEL WITH SCREEN*

*MEDICAL DEVICE AND CONTROL PANEL WITH SCREENS*

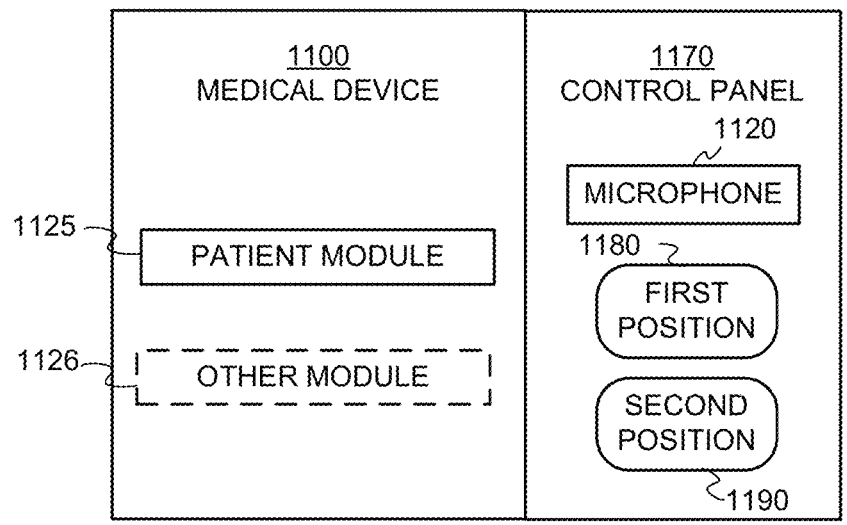
FIG. 11  *MEDICAL DEVICE AND ATTACHED CONTROL PANEL WITH MICROPHONE*

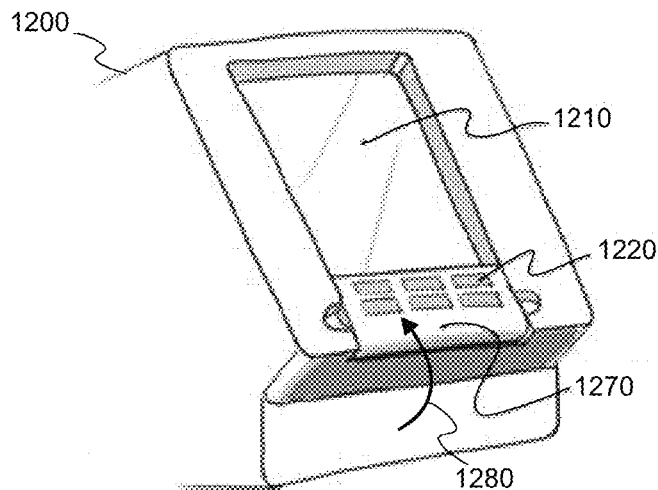
FIG. 12A <u>MEDICAL DEVICE WITH CONTROL PANEL IN CLOSED POSITION</u>
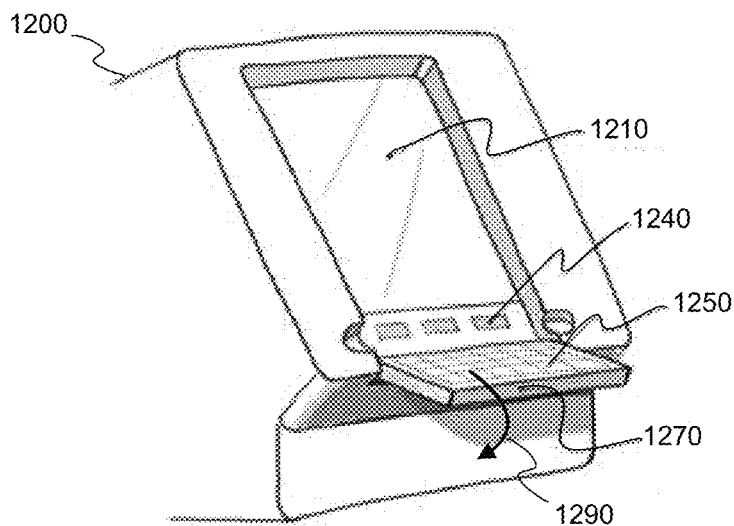
FIG. 12B <u>MEDICAL DEVICE WITH CONTROL PANEL IN OPEN POSITION</u>

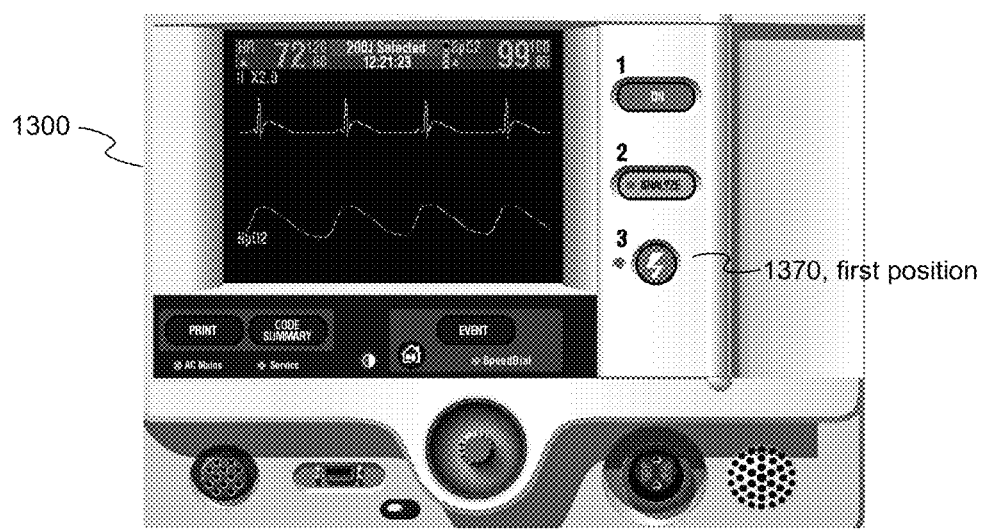
FIG. 13A <u>MEDICAL DEVICE WITH CONTROL PANEL IN CLOSED POSITION</u>
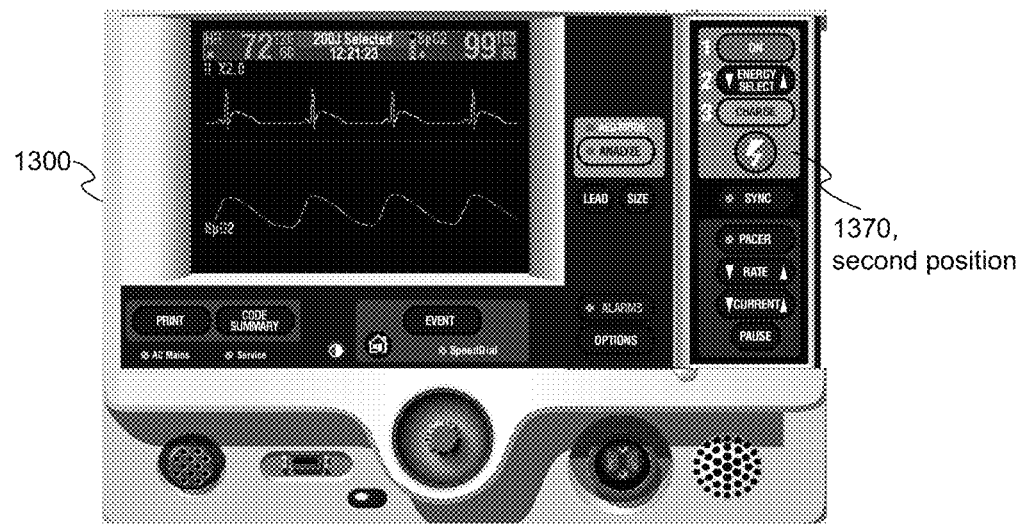
FIG. 13B <u>MEDICAL DEVICE WITH CONTROL PANEL IN OPEN POSITION</u>

*METHOD OF TREATING A PATIENT AND MONITORING A PATIENT USING A MEDICAL DEVICE*

MEDICAL DEVICE WITH INTERACTIVE CONTROL PANEL

CROSS-REFERENCE TO RELATED PATENT APPLICATIONS

This patent application may be found to be related to U.S. patent application Ser. No. 13/589,911, filed on the same day as the instant application, with the same inventor and on behalf of the same assignee.

FIELD

This invention generally relates to external defibrillators.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

During VF, the person's condition deteriorates, because the blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

Advanced medical devices can actually coach a rescuer who performs CPR. For example, a medical device can issue instructions, and even prompts, for the rescuer to perform CPR more effectively.

Referring again to the external defibrillators described above, these medical devices can provide quick treatment and monitoring to patients suffering from various cardiac conditions like VF. External defibrillators can provide defibrillation therapy to a patient suffering from VF and can also monitor and give feedback to a user about the conditions from which the patient is suffering so that proper treatment can be administered. Some operators, especially those with little or no experience, may find external defibrillators to be difficult to use. One known aid for using external defibrillators is to automate some functions of the device so that a less experienced or even a very inexperienced user can use the device to treat and/or monitor a patient within the critical time period for receiving treatment. Such devices are usually operable in two modes—an automated mode for unskilled users and a manual mode designed for operation by skilled users. It is difficult to provide multiple sets of interfaces on an external defibrillator for different skill levels of users, however, because space is very limited.

Embodiments of the invention address these and other limitations of the prior art.

BRIEF SUMMARY

The present description describes medical devices, systems, software and methods, the use of which may help overcome problems and limitations of the prior art.

In one embodiment, a medical device includes a housing, a patient module located within the housing and a control panel attached to the housing. The medical device can be used for treating and/or monitoring one or more parameters of a patient. The patient module performs the treatment and monitoring functions. The control panel has a first surface and a second surface. The control panel is positionable between a first position with respect to the housing that exposes the first surface to a user, and a second position that exposes the second surface to the user. A set of user controls is located on at least one of the first surface and the second surface, and is structured to allow the user to interact with the patient module.

In another example, methods of treating and/or monitoring a parameter of a patient using the disclosed medical devices are also disclosed. Such methods detect that the control panel of the medical device is in the first position, which exposes the first set of user controls. When the control panel is in the first position, user input is accepted from the first set of user controls to interact with the patient module. Optionally, the disclosed methods may also detect that the control panel is in the second position and user input may be accepted from the second set of user controls when the control panel is in the second position.

These and other features and advantages of this description will become more readily apparent from the following Detailed Description, which proceeds with reference to the drawings, in which:

BRIEF DESCRIPTION OF THE DRAWINGS

FIG. 1 is a diagram of a scene where an external defibrillator is used to save the life of a person according to embodiments.

FIG. 2 is a table listing two main types of the external defibrillator shown in FIG. 1, and who they might be used by.

FIG. 4 is a block diagram of a medical device with an attached control panel that has a first operable position and a second operable position according to embodiments.

FIG. 5 is a block diagram of a first and second surface of a control panel according to embodiments.

FIG. 7 is a conceptual diagram of a medical device with a control panel that can be positioned in at least two positions with respect to the medical device in accordance with embodiments.

FIG. 8 shows an embodiment of the medical device of FIG. 7 where the control panel is attached to the medical device with hinges.

FIG. 11 shows another embodiment of the device of FIG. 7, where the control panel has a microphone.

FIG. 12A shows an embodiment of a medical device with an attached control panel in the closed position.

FIG. 12B shows the embodiment of the medical device of FIG. 12A with the attached control panel in the open position.

FIG. 13A shows another embodiment of a medical device with an attached control panel in the closed position.

FIG. 13B shows the medical device of FIG. 13A with the attached control panel in the open position.

DETAILED DESCRIPTION

Figure 3:
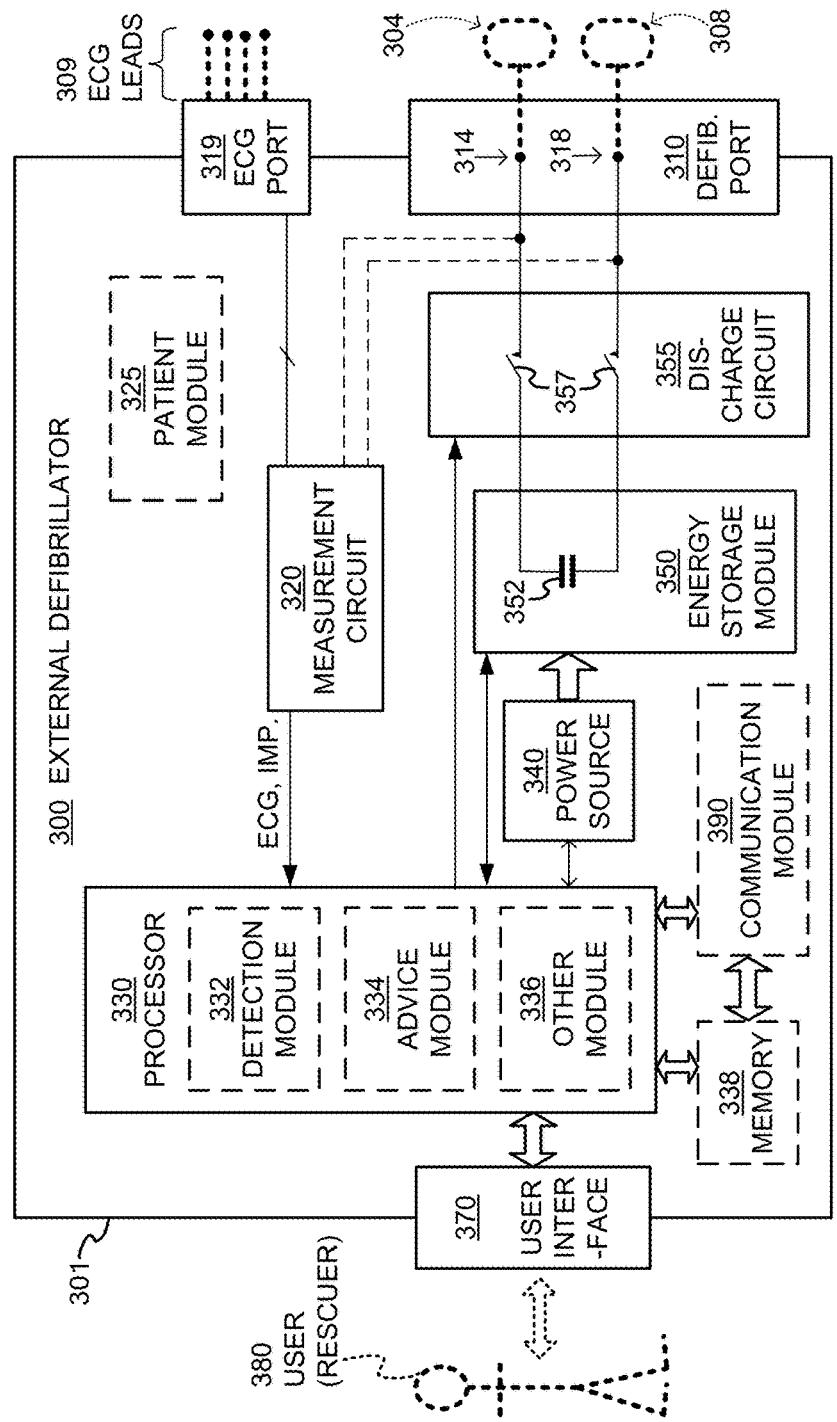
FIG. 3 is a diagram showing components of an external defibrillator, such as the one shown in FIG. 1, which is made according to embodiments.

As has been mentioned, the present description is about external defibrillators. More specifically, the disclosure includes devices, control systems, software, and methods for treating a patient and monitoring various parameters of a patient with external defibrillators. Example embodiments are now described in more detail.

FIG. 1 is a diagram of a defibrillation scene. A person 82 is lying on their back. Person 82 could be a patient in a hospital, or someone found unconscious, and then turned to be on their back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100, and are sometimes called electrodes 104, 108. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

FIG. 2 is a table listing two main types of external defibrillators, and who they are primarily intended to be used by. A first type of defibrillator 100 is generally called a defibrillator-monitor, because it is typically formed as a single unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

There are additional types of external defibrillators, which are not listed in FIG. 2. For example, a hybrid defibrillator can have aspects of an AED, and also of a defibrillator-monitor. A usual such aspect is additional ECG monitoring capability.

FIG. 3 is a diagram showing components of an external defibrillator 300 made according to embodiments. These components can be, for example, in external defibrillator 100 of FIG. 1. Plus, these components of FIG. 3 can be provided in a housing 301, which is also known as casing 301.

External defibrillator 300 is intended for use by a user 380, who would be the rescuer. Defibrillator 300 typically includes a defibrillation port 310, such as a socket in housing 301. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as will be seen later in this document.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or from a different number of leads. Moreover, a defibrillator-monitor could have additional ports (not shown), and a patient module 325 for the above described additional features, such as patient signals.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions. In addition, patient module 325 is indeed provided, it may be operated in part by processor 330, etc. Patient module 325 may be used to treat a patient such as by administering defibrillation and monitoring a parameter of a patient such as by detecting and displaying the ECG of a patient, for example.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, and so on.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for user 380. User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

Referring now to FIG. 4, a medical device 400 is disclosed for a user that treats a patient, monitors parameters of a patient, or both. Treatment of a patient can include administering medical care, such as defibrillation therapy and the like. Monitoring parameters of the patient can include monitoring the patient's pulse, heart rate, blood pressure, breathing, and the like. In FIG. 4, the medical device includes a housing 401 and a patient module 425 located within the housing 401. The patient module 425 provides the ability to both treat and/or monitor parameters of the patient. Optionally, one or more other modules 426 may also be located within the housing to perform other desired functions such as defibrillation, pacing, or interacting with patient data such as analyzing, storing, or transferring the data, for example.

The medical device 400 shown in FIG. 4 also includes a control panel 470 that is attached to the housing 401. The control panel 470 includes a first surface and a second surface (not shown) and is positionable between a first position 480 and a second position 490 with respect to the housing 401 of the medical device 400. The first position 480 exposes the first surface of the control panel 470 to a user of the medical device 400 and the second position 490 exposes the second surface of the control panel 470 to the user of the medical device 400. User controls are located on one or the other or both of the first surface and the second surface of the control panel 470 and are each structured to interact with the patient module 425. The user controls are structured to allow the user to interact with the patient module 425 and optionally any other modules 426, if present, of the medical device 400. For example, FIG. 4 shows a control panel 470 in which the first position 480 of the control panel 470 exposes a first set of user controls 482 to the user and the second position 490 of the control panel 470 exposes a second set of user controls 492 to the user. This example shows that at least one of the positions of the control panel 470 exposes a set of user controls to the user so the user can interact with the patient module 425. In the examples in which user controls 482, 492 are exposed to the user in both the first position 480 and the second position 490 of the control panel 470, the user controls 482, 492 can include some or all of the same control functions or can include entirely different control functions.

For example, FIG. 5 shows an exemplary first surface 500 and a second surface 501 of a control panel of the disclosed medical devices. The first surface 500 includes three user controls 502, 504, and 506 and the second surface 501 includes four user controls 508, 510, 512, and 514. When the control panel changes position from exposing the first surface 500 to exposing the second surface 501 to the user, the user controls associated with each of the first surface 500 and the second surface 501 are available for the user to interact with the patient module to treat and monitor parameters of the patient. In this example, the user controls 502, 504, and 506 of the first surface 500 of the control panel and the user controls 508, 510, 512, and 514 of the second surface 501 of the control panel include at least one differing user control. As discussed above, in other examples, the user controls exposed in the first position and the second position of the control panel may differ to a larger extent.

Figure 6:
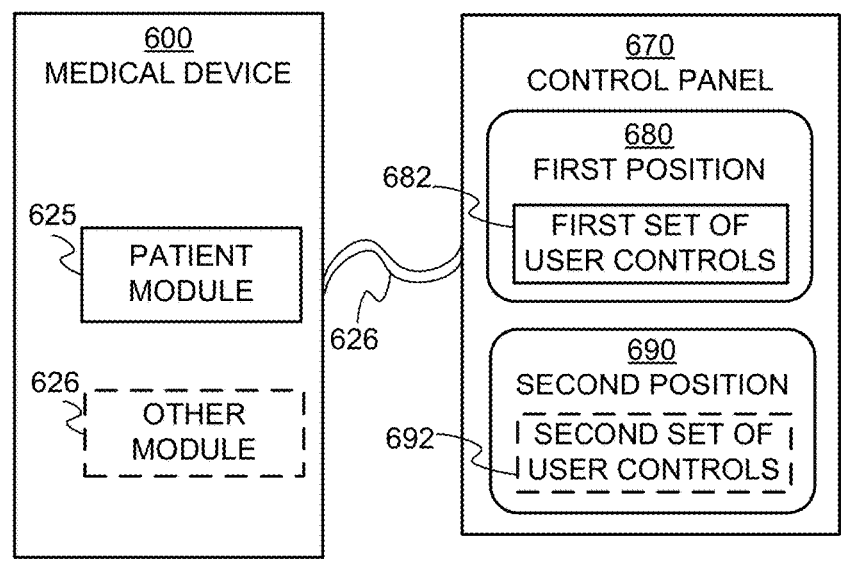
FIG. 6 is a block diagram of a medical device with a control panel attached together with a cable according to embodiments.

FIGS. 6-8 are examples of medical devices with their respective control panels attached to the housing in various manners. In each of these examples, respective patient modules 625, 725, and 825 and optionally other modules 626, 726, and 826, if desired, are located within the housing of the medical devices 600, 700, and 800. The respective control panels 670, 770, and 870 are positionable in respective first positions 680, 780, and 880 and second positions 690, 790, and 890 to expose respective first sets of user controls 682, 782, and 892 in the first positions 680, 780, and 880 and second sets of user controls 692, 792, and 892 in the second positions 690, 790, and 890. The control panel 670 in FIG. 6 is attached to the housing of the medical device 600 with a cable 626. FIG. 7 shows the control panel 770 attached directly to the housing of the medical device 700. FIG. 8 shows the control 870 attached directly to the housing of the medical device 800 by two hinges 828. Any number of hinges can be included to movably attach the control panel 870 to the housing of the medical device 800. The control panel 870 is positionable between the first position 880 and the second position 890 by being rotated around the hinges 828 in the example medical device shown in FIG. 8, or any other suitable number of hinges in other embodiments. In the examples in which the control panel is attached to the housing of the medical device with one or more hinges, the control panel may also be electrically coupled to the patient module by an electrical connection that passes through some portion of the hinge(s).

In an alternative embodiment, the housing of the control panel includes a recess or other area in which to store or house the control panel. The control panel can be retrieved from the recess or other storage area within the housing so that the user can interact with the patient module through the user controls on the first surface and second surface of the control panel. The control panels in these examples are attached to the housing of the medical device in any suitable manner so that the first surface can expose a first set of user controls to the user and the second surface can expose a second set of user controls to the user. For example, the control panel is attached to the housing of the medical device with a cable and is stored within a recess of the housing. The cable can be selectively attached to the control panel and/or the device to permit the user to replace the control panel for any reason. For example, the control panel may need to be repaired or a newer model may replace an older control panel. In one example medical device, the control panel presents user controls to the user in one language and may need to be replaced with user controls in another language. In another example, the first surface of the control panel has user controls that enable the medical device to be used in a first mode, such as an automatic defibrillation mode, and the second set of user controls enables the medical device to be used in second mode, such as a manual defibrillation mode. In another example, the first set of user controls is presented in English or any other language and the second set of user controls is presented in Spanish or any language other than English. Any suitable differences may be incorporated into the first and second sets of user controls. In still other examples, the first surface of the control panel and/or the first set of user controls include a first color and the second surface of the control panel and/or the second set of user controls includes a second color that is different than the first color. The coloring may differ so that one of the surfaces and/or sets of user controls are the same color as the medical device housing and the other surface and/or set of user controls is a color different from the medical device housing. The differences in the first set or user controls and the second set of user controls can be associated with different levels of skill of the user so that the differences aid the less advanced user in operating the medical device or the color differences make it easy for users to determine whether the control panel is exposing the first set of user controls or the second set of user controls.

Any of the user controls described above can include one or more of tactile feedback and audible feedback. Tactile feedback is any form of feedback that is perceptible by touch or is tangible for the user. Audible feedback includes audible instructions for performing a task or operating the medical device, confirmation that input from the user was received or that data was sent from the medical device to another entity, such as a hospital or medical facility, or the like. Any suitable tactile and audible feedback may be included in the medical device. In some examples, the user receives an audible confirmation that the control panel of the medical device is positioned in either the first position or the second position. Such a confirmation may be important when the first set of user controls exposed when the control panel is in the first position and the second set of user controls exposed when the control panel is in the second position offer different functionality and/or are best suited for users with different skill levels in operating the medical device, for example. The user controls may also include an alphanumeric keypad or other keyboard-type data entry user control.

Figure 9:
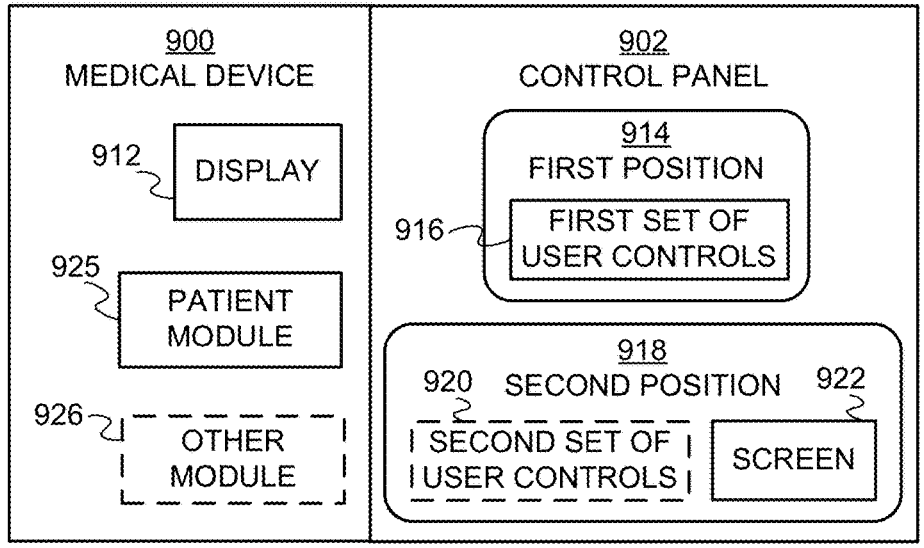
FIG. 9 shows an embodiment of the device of FIG. 7, where the control panel further has a screen.
Figure 10:
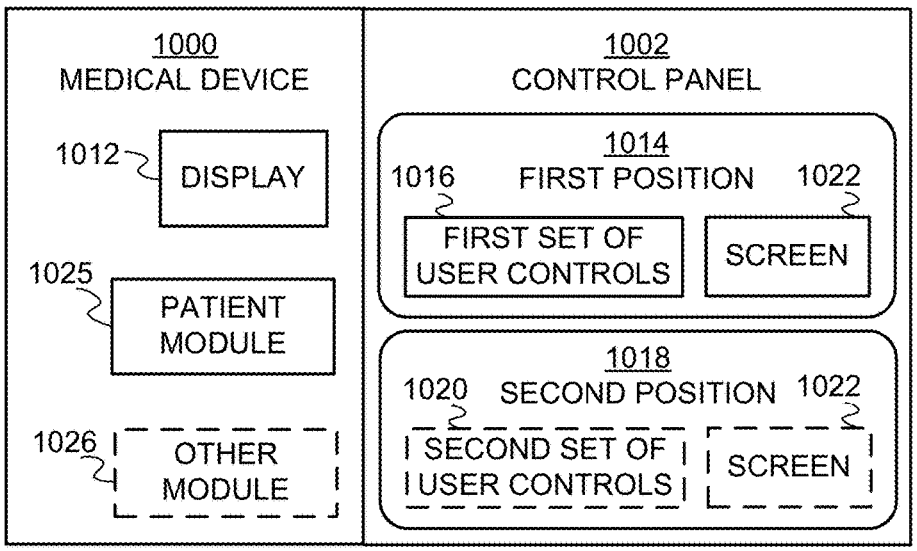
FIG. 10 shows an embodiment of the device of FIG. 7, where control panel has two screens.

Referring now to FIGS. 9 and 10, one or both of the sets user controls of the control panel can include a screen. For example, FIG. 9 includes a medical device 900 with an attached control panel 902. The medical device includes a display 912, a patient module 925, and optionally another module 926 that provides additional functionality, if desired. When the control panel 902 is in a first position 914, the first set of user controls 916 is exposed to the user, in a manner similar to that described above. When the control panel 902 is in the second position 918, a screen 922 and optionally a second set of user controls 920 is exposed to the user. The screen 922 can be the only user control exposed to the user when the control panel 902 is in the second position 918 or any other type of user interface can be included in the additional user controls, if desired.

FIG. 10 illustrates a block diagram of another embodiment of a medical device 1000 with an attached control panel 1002. Similar to FIG. 9, the medical device 1000 includes a display 1012, a patient module 1025, and optionally another module 1026 that provides additional functionality, if desired. However, in FIG. 10, when the control panel 1002 is in the first position 1014, the first set of user controls 1016 and a screen 1022 are exposed to the user. When the control panel 1002 is in the second position 1018, a second set of user controls 1020 and a screen are optionally 1022 exposed to the user. In this embodiment, the second set of user controls 1020 and the screen 1022 may or may not be exposed to the user when the control panel 1002 is in the second position 1018. Further, the control panel 1002 may or may not expose any user controls when the control panel 1002 is in the second position 1018. The displays 912, 1012 of the medical devices 900, 1000 shown in FIGS. 9 and 10 can be any suitable display that presents data, information, or other output to the user.

The screens 922, 1022 shown in FIGS. 9 and 10 can be structured to display one or more parameters that are associated with the respective position of the control panels 902, 1002. For example, the screen 1022 in FIG. 10 that is exposed when the control panel 1002 is in the first position 1014 can be structured to display one or more parameters that are associated with the first set of user controls 1016. The screen 1022 exposed when the control panel 1022 is in the second position 1014 also can be structured to display one or more parameters associated with the second set of user controls 1020. Any of the disclosed screens can be a touch screen or other screen that receives user input, such as a screen that receives user input with a stylus or other writing utensil. The touch screen can receive a user's signature or other written input by either a finger or other writing utensil like the stylus discussed above. The touch screen can also receive any other type of user action, such as tapping and input received from a soft key display. Alternatively or in addition to a touch screen, the user controls on the control panel when it is in one or both of the first position and the second position may include an alphanumeric keypad. The alphanumeric keypad may receive input from the user that appears directly or is analyzed and appears in another form on the display of the medical device or prompts the medical device to perform a desired function.

In still other examples, such as the medical device 1100 shown in FIG. 11, the medical device 1100 includes a patient module 1125 and another optional module 1126 having any other desired functionality. The control panel 1170 is attached to the medical device and is positionable in a first position 1180 and a second position 1190, in a similar manner to the medical devices described above. The control panel 1170 in this example also includes a microphone 1120 that receives audio input from a user, the patient, or from the ambient environment surrounding the patient.

The disclosed medical devices include a detector in some examples. The detector detects the position of the control panel. For example, the detector can detect when the control panel is in the first position and the second position, respectively. The detector can also detect when the control panel is not positioned properly in either the first position or the second position and may prompt the user to properly position the control panel in the first position or the second position for use. A processor in the medical device can operate a first protocol when the control panel is detected to be in the first position and a second protocol when the control panel is detected to be in the second position. A processor in the medical device, such as the processor shown in FIG. 3, may be responsive to an output from the detector detecting whether the control panel is in the first position or the second position.

Whether or not a detector is present, the first set of user controls can receive power to be activated when the control panel is positioned in the first position and/or the second set of user controls can receive power to be activated when the control panel is positioned in the second position. The first set of user controls may be deactivated when the control panel is in the second position and the second set of user controls may be deactivated when the control panel is in the first position. The position of the control panel may be detected by any suitable means, such as the detector described above, the activation or use of any one of the user controls in either the first set of user controls or the second set of user controls, or any other suitable manners.

The first set of user controls on the medical device can be associated with functions of the medical device that are operable by a user having a first skill level and the second set of user controls can be associated with functions of the medical device that are operable by a user with a second skill level that is different than the first skill level associated with the first set of user controls. The second skill level is more advanced than the first skill level, in some examples. In some embodiments, the patient module is a defibrillation module. When the control panel is positioned in the first position, the first set of user controls enables the medical device to be used in an automatic defibrillation mode and the second set of user controls enables the medical device to be used in a manual defibrillation mode. Typically, the skill level required to operate the medical device in a manual defibrillation mode is more advanced than the skill level required to operate the medical device in an automatic defibrillation mode.

For example, FIGS. 12A and 12B show a medical device 1200 with an attached control panel 1270 in a first position 1280 and a second position 1290, respectively. The medical device includes a display 1210 in this example for displaying various data, images, text, and other information to the user. The first position 1280 corresponds to the control panel 1270 being positioned in a "closed" position in which the control panel is positioned flat against the medical device and exposes a first set of user controls 1220. The second position 1290 corresponds to the control panel 1270 being positioned in an "open" position in which the control panel is rotated open to expose a second set of user controls 1240, 1250. The second set of user controls includes user controls 1240 and a keypad-type user input 1250. The second set of user controls provides more available controls than the first set of user controls and may be designed for operation by users with more advanced skill levels in operating the medical device than the first set of user controls.

FIGS. 13A and 13B show another example medical device 1300 in which the control panel 1370 is positioned in the first position and the second position, respectively. When the control panel 1370 is in the first position, three user controls are exposed to the user and when the control panel 1370 is in the second position, fourteen user controls are exposed to the user including the three user controls from the first position. In this example, the skill level of the user that is required to operate the medical device when the control panel 1370 is in the second position and the second set of user controls is exposed is more advanced than the skill level of the user that is required to operate the medical device when the control panel 1370 is in the first position and the first set of user control is exposed.

The disclosed medical devices may include optional features such as a housing metal contact that is coupled to and extends away from the housing and a control panel metal contact that is coupled to the control panel. The housing metal contact and the control panel metal contact may be in continuous contact with each other when the control panel is positioned in the first position, the second position, and therebetween. In another example, the housing metal contact and the control panel metal contact are in contact with each other when the control panel is in the second position and not in contact with each other when in the first position, and vice versa. These metal contacts can detect the position of the control panel.

The disclosed medical devices may also include a securing mechanism that secures the control panel in one or both of the first and the second positions. Alternatively, a first securing mechanism secures the control panel in the first position and a second securing mechanism secures the control panel in the second position. The securing mechanisms include any electrical, mechanical, or other type of mechanism that retains the control panel in a particular position.

Figure 14:
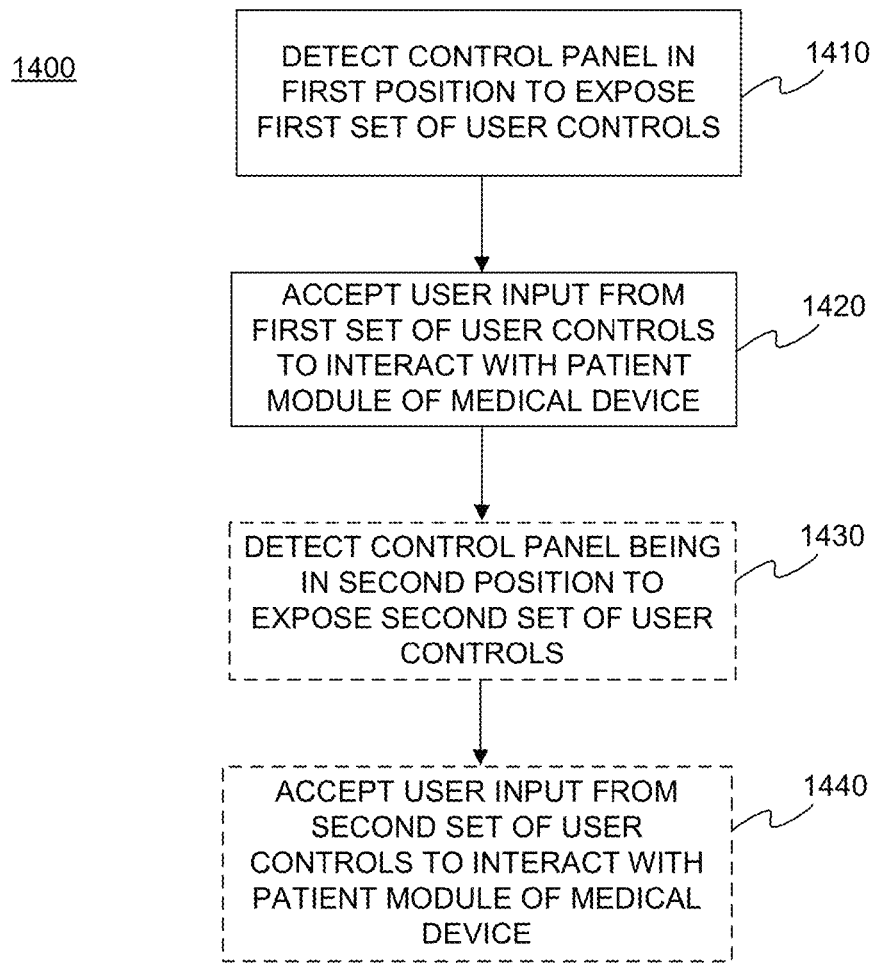
FIG. 14 is a flowchart for illustrating methods according to embodiments.

Referring now to FIG. 14, a method 1400 of at least one of treating a patient and monitoring parameters of a patient using a medical device are disclosed. The method uses one of the medical devices described above and detects that the control panel is in a first position in a first operation 1410. Having the control panel in the first position exposes a first set of user controls to the user. When the control panel is detected in the first position, the medical device then accepts user input from the first set of user controls to permit the user to interact with the patient module of the medical device in an operation 1420. Optionally, the method 1400 also detects that the control panel is in the second position in an operation 1430, which exposes a second set of user controls to the user. When the control panel is detected in the second position, the medical device then accepts user input from the second set of user controls to interact with the patient module. Accepting the user input from either of the first set of user controls or the second set of user controls may include making a selection to control the patient module of the medical device.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems.

The following claims define certain combinations and subcombinations of elements, features, steps, and/or functions, which are regarded as novel and non-obvious. Additional claims for other combinations and subcombinations may be presented in this or a related document.

What is claimed is:

1. A medical device for treatment and monitoring of one or more patient parameters, comprising:
   a housing;
   a patient module located within the housing, the patient module configured to treat a patient and monitor a patient parameter;
   a control panel attached to the housing, the control panel having a first surface and an integral and opposing second surface, the first surface including a first screen, the control panel structured to be positioned in either a first position with respect to the housing in which the first surface and the first screen are exposed to a user or a second position with respect to the housing in which the opposing second surface is exposed to the user;
   a first set of user controls located on the first surface of the control panel, the first set of user controls structured to allow the user to interact with the patient module to one or both of treat the patient or monitor the patient parameter, and the first screen structured to display one or more parameters associated with the first set of user controls; and
   a second set of user controls located on the second surface of the control panel, the second set of user controls structured to allow the user to interact with the patient module to one or both of treat the patient or monitor the patient parameter.

2. The device of claim 1, in which the control panel is structured to be positioned between either the first position or the second position by retrieving the control panel from a recess within the housing.

3. The device of claim 2, in which when the control panel is positioned in the first position, the first set of user controls enables the medical device to be used in an automatic defibrillation mode and when the control panel is in the second position, the second set of user controls enables the medical device to be used in a manual defibrillation mode.

4. The device of claim 2, in which when the control panel is positioned in the first position, the first set of user controls is in a first language and when the control panel is positioned in the second position, the second set of user controls is in a second language different from the first language.

5. The device of claim 1, in which the control panel is attached to the housing by at least one hinge and the control panel is electrically coupled to the patient module by an electrical connection that passes through at least a portion of the hinge.

6. The device of claim 1, in which the control panel is attached to the housing by a cable.

7. The device of claim 1, in which the first set of user controls receives power to be activated when the control panel is positioned in the first position, and in which the first set of user controls is deactivated when the control panel is positioned in the second position.

8. The device of claim 1, in which the first set of user controls includes a microphone.

9. The device of claim 1, in which the first set of user controls includes tactile feedback.

10. The device of claim 1, in which the first set of user controls includes an audible feedback when the control panel is positioned in the first position.

11. The device of claim 1, in which the first screen is a touch screen that is structured to detect user action and display a soft key for action by the user.

12. The device of claim 1, in which the second surface of the control panel includes a second screen that is exposed to the user when the control panel is in the second position, the second screen structured to display one or more parameters associated with the second set of user controls.

13. The device of claim 1, in which the first set of user controls is associated with functions of the medical device operable by a user with a first skill level, and in which the second set of user controls are associated with functions of the medical device which are operable by a user with a second skill level that is more advanced than the first skill level.

14. The device of claim 1, in which the patient module is a defibrillation module,
   when the control panel is positioned in the first position, the first set of user controls enables the medical device to be used in an automatic defibrillation mode,
   and when the control panel is positioned in the second position, the second set of user controls enables the medical device to be used in a manual defibrillation mode.

15. A method of one of treating a patient and monitoring a parameter of the patient using a medical device which includes a housing, a patient module located within the housing for the one of treating the patient and monitoring the patient parameter, a control panel attached to the housing, the control panel having a first surface and an integral and opposing second surface, the first surface includes a first screen, the control panel structured to be positioned in either a first position with respect to the housing in which the first surface and the first screen are exposed to the user or a second position with respect to the housing in which the opposing second surface is exposed to the user; and a first set of user controls located on the first surface of the control panel and a second set of user controls located on the second surface of the control panel, the first set of user controls and the second set of user controls structured to allow the user to interact with the patient module to one or both of treat the patient or monitor the patient parameter, and the first screen structured to display one or more parameters associated with the first set of user controls, the method comprising:
   detecting the control panel being in the first position to expose the first set of user controls and the first screen;
   accepting user input from the first set of user controls to interact with the patient module to one or both of treat the patient or monitor the patient parameter, the first set of user controls located on the first surface;
   accepting user input from the second set of user controls to interact with the patient module to one or both of treat the patient or monitor the patient parameter, the second set of user controls located on the second surface of the control panel; and
   displaying the one or more parameters associated with the first set of user controls on the first screen.

16. The method of claim 15 further comprising:
   detecting the control panel is in the second position to expose the second set of user controls; and
   accepting user input from the second set of user controls to interact with the patient module to one or both of treat the patient or monitor the patient parameter.

17. The method of claim 15, in which accepting the user input from the first set of user controls to interact with the patient module comprises accepting user input that makes a selection to control the patient module.

18. The method of claim 15, in which accepting the user input from the first set of user controls comprises displaying a representation of data generated by the patient module on the first screen.

* * * * *